(12) United States Patent
Husheer

(10) Patent No.: US 9,562,811 B2
(45) Date of Patent: Feb. 7, 2017

(54) TEMPERATURE SENSOR STRUCTURE

(75) Inventor: Shamus Husheer, Cambridge (GB)

(73) Assignee: Cambridge Temperature Concepts Limited, Cambridge (GB)

( * ) Notice: Subject to any disclaimer, the term of this patent is extended or adjusted under 35 U.S.C. 154(b) by 1111 days.

(21) Appl. No.: 13/061,191

(22) PCT Filed: Aug. 27, 2009

(86) PCT No.: PCT/EP2009/061096
§ 371 (c)(1),
(2), (4) Date: Mar. 21, 2011

(87) PCT Pub. No.: WO2010/023255
PCT Pub. Date: Mar. 4, 2010

(65) Prior Publication Data
US 2011/0301493 A1   Dec. 8, 2011

(30) Foreign Application Priority Data

Aug. 28, 2008   (GB) .................................. 0815694.5

(51) Int. Cl.
*G01K 1/16*   (2006.01)
*G01K 7/42*   (2006.01)
*G01K 13/00*   (2006.01)

(52) U.S. Cl.
CPC ................. *G01K 1/16* (2013.01); *G01K 1/165* (2013.01); *G01K 7/42* (2013.01); *G01K 13/002* (2013.01)

(58) Field of Classification Search
CPC ........ G01K 1/16; G01K 13/002; G01K 1/165; G01K 7/42

USPC ......................................................... 600/549
See application file for complete search history.

(56) References Cited

U.S. PATENT DOCUMENTS

| | | | | |
|---|---|---|---|---|
| 4,929,089 | A | * | 5/1990 | Tsuchida ......................... 374/44 |
| 5,816,706 | A | * | 10/1998 | Heikkila et al. .............. 374/134 |
| 6,220,750 | B1 | | 4/2001 | Palti |
| 6,595,929 | B2 | * | 7/2003 | Stivoric et al. ............... 600/549 |
| 8,057,093 | B2 | * | 11/2011 | Sattler ........................... 374/100 |
| 2006/0173375 | A1 | * | 8/2006 | Koch ............................. 600/549 |
| 2007/0295713 | A1 | * | 12/2007 | Carlton-Foss ................ 219/497 |
| 2008/0170600 | A1 | * | 7/2008 | Sattler et al. ................. 374/163 |
| 2010/0121217 | A1 | * | 5/2010 | Padiy et al. .................. 600/549 |

FOREIGN PATENT DOCUMENTS

JP   2008076144 A   4/2008

OTHER PUBLICATIONS

English Translation of Examination Report dated Apr. 8, 2014.

* cited by examiner

*Primary Examiner* — Rene Towa
(74) *Attorney, Agent, or Firm* — Vorys, Sater, Seymour and Pease LLP; Vincent M DeLuca

(57) ABSTRACT

A device for measuring temperature comprising: first and second temperature sensors enclosed in a first material having one or more material components; a contact surface for contacting a body whose temperature is to be measured, at least part of the contact surface being parallel to a lateral direction; wherein the first and second temperature sensors are arranged at different depths from the contact surface and the net thermal conductivity across the device from the contact surface through the first and second temperature sensors is greater than the net lateral thermal conductivity of the device through the first and second temperature sensors.

18 Claims, 2 Drawing Sheets

TEMPERATURE SENSOR STRUCTURE

BACKGROUND OF THE INVENTION

This invention relates to a device for measuring temperature, particularly the temperature of an animal or human body.

Sensors for measuring temperature are well known and include thermistors, thermocouples and semiconductor-based electronic sensors. If correctly calibrated, such sensors can provide an indication of the temperature of an object in the region from which the sensor takes its inputs. For example, a thermistor placed in direct contact with an object will give an indication of the temperature of that part of the object with which the sensor is in contact.

Often, an object does not have a uniform temperature and its measured temperature varies throughout its volume. For example, the temperature of an animal or human typically varies from its core body temperature to skin temperature. Skin temperature can vary considerably with environmental conditions and it is therefore the core body temperature which is typically more important for medical and diagnostic applications. However, it is not always possible or convenient to measure core body temperature directly by invasive means. It is preferable to make one or more measurements of an easily accessible part of the body (such as skin temperature) and estimate core body temperature from those measurements.

US Patent Application No. 2007/0282218 discloses a device for measuring the local temperature of an external surface of a body using at least two temperature sensors separated by an insulating layer. The measurements may be used to calculate core body temperature by correcting for a difference between core body temperature and local temperature. Algorithms for performing such a correction in dependence on known thermal characteristics of the body are well known in the art (for example, see "Computation of mean body temperature from rectal and skin temperatures", *Journal Applied Physiology* 31: 484-489, 1971).

An example of a conventional device 12 for measuring the temperature of a body 11 is shown in FIG. 1. Temperature sensors 13 and 14 are arranged at different distances from the external surface 18 of body 11 in material 15, and are separated by a thermally-insulating barrier 16. The effect of thermally-insulating barrier 16 is to cause temperature sensors 13 and 14 to attain different equilibrium temperatures at different rates, such that a measurement of the temperature of body 11 can be estimated from the heat flow across the device between the first and second sensors.

Conventional devices measure the heat flow from the subject body into the device and require that the temperature sensors are accurately positioned so as to properly capture the flow of heat across the device. The accuracy of such devices is therefore heavily dependent on the accuracy of placement of the sensors of the device. Furthermore, the devices are readily influenced by other sources of heat in their environment.

There is therefore a need for a device for measuring temperature whose accuracy is less dependent on the accuracy of placement of its temperature sensors and the proximity of other sources of heat in its environment.

SUMMARY OF THE INVENTION

According to a first aspect of the present invention there is provided a device for measuring temperature comprising: first and second temperature sensors enclosed in a first material having one or more material components; a contact surface for contacting a body whose temperature is to be measured, at least part of the contact surface being parallel to a lateral direction; wherein the first and second temperature sensors are arranged at different depths from the contact surface and the net thermal conductivity across the device from the contact surface through the first and second temperature sensors is greater than the net lateral thermal conductivity of the device through the first and second temperature sensors.

Suitably, said first material has an anisotropic thermal conductivity. Preferably the thermal conductivity of the first material has an anisotropy ratio of at least 2. Preferably the first material has a maximum thermal conductivity of at least 0.5 W/mK.

Optionally, the device further comprises a second material at least partially enclosing the first material and having a lower thermal conductivity in the lateral direction than the first material. Preferably the first material has a greater thermal conductivity than the second material in the lateral direction by a factor of at least 4.

According to a second aspect of the present invention there is provided a device for measuring temperature comprising: a first material having one or more material components; first and second temperature sensors embedded in the first material; a second material at least partially enclosing the first material and having a lower thermal conductivity than the first material; and a contact surface for contacting a body whose temperature is to be measured, at least part of the contact surface being parallel to a lateral direction; wherein the first and second temperature sensors are arranged at different depths from the contact surface and the first and second materials are arranged such that the net thermal conductivity across the device from the contact surface through the first and second temperature sensors is greater than the net lateral thermal conductivity of the device through the first and second temperature sensors.

The second material may completely enclose the first material. Preferably the second material is thicker over the lateral extremities of the first material than over the contact surface and its opposing surface. Preferably the first material is substantially disc-shaped and the plane of the disc is substantially parallel with the lateral direction. Preferably the second material forms a ring-shaped annulus about the disc-shaped first material, the plane of the ring being substantially coincident with the plane of the disc.

Each depth may be a distance from the contact surface to the respective temperature sensor along an axis substantially perpendicular to the contact surface. Alternatively, each depth is a thermal depth defined by the net thermal conductance from the contact surface to the respective temperature sensor. The first and second temperature sensors may be at the same distance from the contact surface along an axis substantially perpendicular to the contact surface.

Preferably a surface of the first material provides at least part of said contact surface.

Optionally, the first material comprises at least first and second material components having different thermal conductivities, the first temperature sensor being embedded in the first material component and the second temperature sensor being embedded in the second material component. Preferably at least part of the contact surface is provided by the first and second material components.

Preferably the net thermal conductivity across the device is lowest in the lateral direction. Preferably the first material is a thermally conductive polymer.

Optionally, the contact surface supports a thin layer having a higher thermal conductivity than the first material. Preferably, in use, a surface of the first material remote from said contact surface is exposed. Optionally, said remote surface supports a thin layer having a higher thermal conductivity than the first material.

DESCRIPTION OF THE DRAWINGS

The present invention will now be described by way of example with reference to the accompanying drawings, in which.

DETAILED DESCRIPTION OF THE DRAWINGS

The following description is presented to enable any person skilled in the art to make and use the invention, and is provided in the context of a particular application. Various modifications to the disclosed embodiments will be readily apparent to those skilled in the art.

The general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

The present invention provides an improved device for measuring temperature and heat flow into or out of a subject body. The device is particularly suitable for measuring the temperature of a human or animal body. A measure of the heat flow from a body combined with a measure of the temperature at the surface of that body allows the calculation of an estimate of a temperature within the body, if one knows something of the thermal characteristics of the body.

For example, the core body temperature (Tcore) of a human or animal may be estimated from a first temperature T1 taken at a first point (such as at the skin) and a second temperature T2 measured at a second point related to the first point by a known thermal transfer function. As is well known in the art, these parameters allow the calculation of the heat flowing out of the skin in this region and can be used to estimate core body temperature Tcore by:

$$Tcore = T1 + A \cdot (T2 - T1)$$

Parameter A is typically an empirically determined coefficient which depends upon the thermal characteristics of the device (the thermal transfer function) and the body tissue. Including higher order terms can further improve the accuracy of this estimate. The thermal characteristics of the device can be straightforwardly selected by design and measured precisely in the laboratory.

Figure 1:
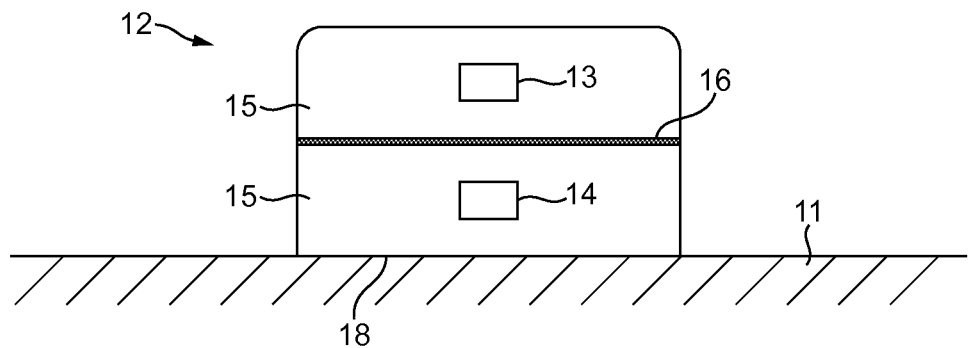
FIG. 1 is a diagram of a prior art device for measuring heat flow from a body.
Figure 2:
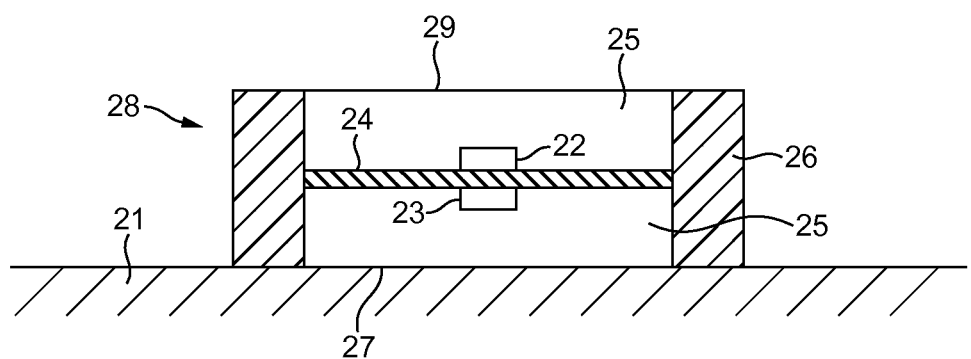
FIG. 2 is schematic diagram of a temperature measuring device in accordance with a first embodiment of the present invention.

FIG. 2 shows a device 28 in accordance with a first aspect of the present invention. Temperature sensors 22 and 23 are mounted on PCB 24, which may or may not extend across the diameter of material component 25 in which it is embedded. PCB 24 is chosen to have a similar thermal conductivity to material 25 such that the effect of its presence on the flow of heat to the first and second temperature sensors 22, 23 is minimised. Indeed, PCB 24 may be omitted if there is some other means of connection to the sensors, in which case material 25 extends between sensors 22 and 23. Material 25 is partially enclosed by material 26, which has a lower thermal conductivity than material 25.

Device 28 is configured such that material 25 provides a contact surface 27 that is adapted to contact the body whose temperature is to be measured (such as the skin of a human). Surface 27 will be referred to herein as the contact surface, and the opposing surface of a device in accordance with the present invention, out of which heat from the body flows, will be referred to as the outer surface. Surface 27 may support an adhesive or other means for attaching the device to the surface of a subject body.

In accordance with the present invention, sensors 22 and 23 are situated at different distances from contact surface 27 such that the sensors are at different distances from body 21 (the source of heat). Preferably sensors 22 and 23 lie on a common axis perpendicular to contact surface 27. This configuration assumes that the vector describing the heat gradient close to the surface of body 21 is normal to that surface.

It is preferable that material 26 does not extend completely over the contact or outer surfaces of the device. It is advantageous if a surface of material 25 forms at least part of contact surface 27 such that the material contacts body 21 in use, and that a surface of material 25 forms at least part of outer surface 27 such that the material is exposed to the environment, allowing heat to flow through the device and out of that surface. Material 26 may enclose material 25 completely, but in this embodiment, it is preferably that material 26 is thinner over the outer and/or contact surface, or be doped in those regions with a more conductive material (such as a metal) so as to increase its conductivity.

One or both of the contact and outer surfaces may support a thin layer (typically less than 1 mm thick) of an additional material (not shown in the figures). This additional material may have a high thermal conductivity (for example, greater than that of material 25 and preferably at least 10 W/mK) so as to efficiently couple (a) the contact surface to the body whose temperature is being measured, and/or (b) the outer surface to the ambient environment. Alternatively, if the additional material is sufficiently thin (preferably less than 0.25 mm), it may have a low thermal conductivity (possibly lower than 1 W/mK) and act as a protective layer for the respective surface, or means for supporting (for example) an adhesive layer.

By adjusting the extent to which insulating material 26 extends over the outer surface of the device, the rates at which the sensors reach their equilibrium temperatures can be varied. It is envisaged that the extent to which the insulating material extends over the outer surface is selected empirically, taking into account the typical range of temperatures expected of the body and environment.

The arrangement of material components 25 and 26 is chosen such that an axis of greatest thermal conductivity across the device is defined. In the embodiment shown in FIG. 2, the axis of greatest thermal conductivity is roughly perpendicular to contact surface 27, through material 25. This is because material 26, which has a lower thermal conductivity, reduces the net thermal conductivity in the directions parallel to contact surface 27 (i.e. laterally). The axis of greatest thermal conductivity is preferably coincident with the direction of heat flow out of body 21. In other words, the direction of the vector describing the flow of heat from body 21 is chosen to be coincident with the direction of highest thermal conductivity of the device when the device is placed in position on the body. In contrast with conventional device configurations, the arrangement of the present invention helps to minimise the leakage of heat to the sensors from the lateral extremities of the device and ensure that it is the heat flow from the core of the body that is measured.

It is advantageous if the thermal conductivity of material 26 is at least 4 times smaller than that of material 25, and preferably at least 10 times smaller. Material 25 preferably has a thermal conductivity of at least 0.5 W/mK. It is particularly advantageous if material 25 is a thermoconductive polymer, such as D8102 manufactured by Cool Polymers which has a thermal conductivity of 3 W/mK. Material 26 is preferably a thermoplastic, such as polyvinyl chloride (PVC) or polyurethane (PU).

Preferably material 25 is substantially disc-shaped having greater extent parallel to surface 27 than normal to surface 27. For example, an appropriate diameter for a patch for the human body is approximately 15 mm, with the two parts of material 25 being approximately 2.5 mm and separated by a PCB disc also 15 mm in diameter and 1 mm thick. Preferably material 26 forms a ring-shaped annulus about material 25, and in the present example is preferably a coating approximately 1 mm thick over material 25.

A device as shown in FIG. 2 may be conveniently manufactured by over-molding the temperature sensors with a thermally conductive polymer, and then over-molding the resulting article with a thermally insulating polymer predominantly in a ring laterally about the disc. In embodiments in which the sensors are mounted on a circuit board, the device may be constructed with a temperature sensor on each side of a printed circuit board. A first over-molding may then be performed using a polymer with thermal characteristics similar to or more conductive than those of the circuit board, and a second over-molding performed using a substantially more insulating polymer. If polymer 25 in which the PCB is embedded is particularly electrically conductive, a thin electrically-insulating layer or film may be employed between the PCB and the conductive polymer.

Figure 3:
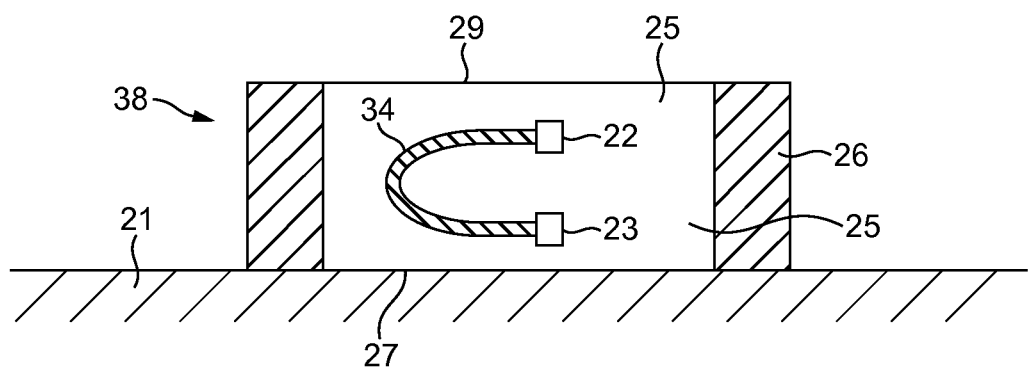
FIG. 3 is a schematic diagram of a temperature measuring device in accordance with a second embodiment of the present invention.

FIG. 3 shows a second embodiment of the present invention in which sensors 22, 23 are mounted on a flexible printed circuit board (PCB) 34. This has two advantages: firstly, device 38 can be flexible, allowing contact surface to better conform to the contours of the external surface of body 21; secondly, by arranging the PCB to bend 180 degrees back upon itself (see FIG. 3), the sensors can be positioned in material 25 such that only material 25 extends between the sensors and the flow of heat past the sensors is not interrupted by the PCB.

Figure 4:
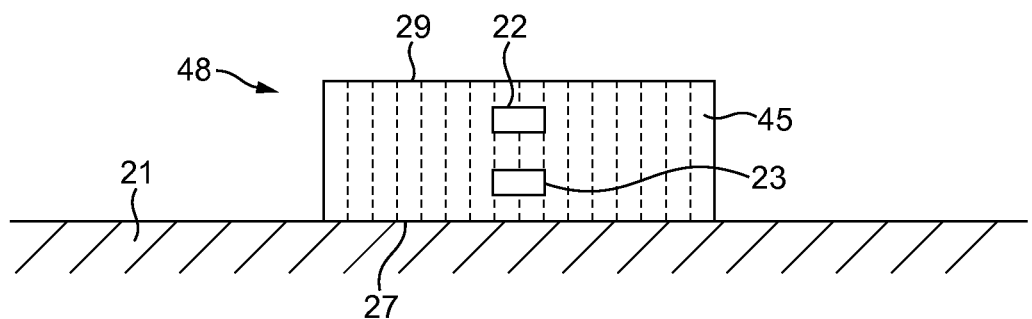
FIG. 4 is a schematic diagram of a temperature measuring device in accordance with a third embodiment of the present invention.

FIG. 4 shows a third embodiment of the present invention in which materials 25 and 26 of devices 28 and 38 are replaced by a single material 45 having an anisotropic thermal conductivity. Material 45 may comprise multiple material components arranged so as to provide the anisotropic thermal conductivity. Sensors 22 and 23 are arranged in material 45 so as to lie substantially along the axis of greatest thermal conductivity of the material and device (indicated by the dashed lines in FIG. 4). Since it is typically desired to capture the flow of heat in a normal direction out of body 21, the axis of greatest thermal conductivity of material 45 will generally be substantially perpendicular to contact surface 27 of device 48.

It is advantageous if the axis of lowest thermal conductivity of material 45 is substantially perpendicular to the axis of greatest thermal conductivity so as to minimise the leakage of heat to the sensors from the lateral portions of the device.

Suitable materials having anisotropic thermal conductivity include thermally conductive polymers having substantially aligned polymer chains and a material matrix of electrically conductive components (such as metal fibres) aligned in a polymeric insulating base material. Preferably material 45 is selected so as to have an anisotropy ratio of at least 2: i.e. the thermal conductivity along the axis of greatest thermal conductivity is at least twice that along a substantially perpendicular axis of lowest thermal conductivity. Most preferably the anisotropy ratio is at least 5. Further advantageously, the thermal conductivity in all directions perpendicular to the axis of greatest thermal conductivity is substantially the same (preferably within 20%).

Contact surface 27 need not be perfectly flat and preferably is adapted to conform to the external surface of the body whose temperature is to be measured. If body 21 is a human or animal body, it is advantageous if a device in accordance with the present invention is flexible so as to allow the contact surface to maintain a good contact with body 21 during movements of the human or animal.

In the above embodiments, it is important that the temperature sensors are at different depths from the contact surface so that each sensor reaches a different equilibrium temperature (as required by the above equation for estimating the core temperature of a body). This depth may be the perpendicular distance from the contact surface to the subject temperature sensor. Alternatively, or additionally, the depth may be defined by the "thermal depth" of the temperature sensor from the contact surface. The thermal depth is the net thermal conductance of the device from the contact surface to the subject temperature sensor and varies with both the distance of the temperature sensor from the contact surface and the thermal conductivity of the intervening material(s).

By arranging for the thermal conductance from the contact surface to be different for each temperature sensor, each temperature sensor will equilibrate at a different temperature. This can be straightforwardly achieved if material 25 comprises a first material component in which a first temperature sensor is enclosed and a second material component in which a second temperature sensor is enclosed, the two material components having different thermal conductivities. Most simply, material 25 can comprise two halves: a first half of the first material component containing the first temperature sensor and a second half of the second material component containing the second temperature sensor, with each material component extending between the respective temperature sensor and the contact surface.

The term "perpendicular distance" as used herein shall be taken to mean the distance from the specified point to the specified surface along the line normal to that surface that passes through that point.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A device for measuring temperature comprising:
   first and second temperature sensors enclosed in a first material having one or more materials;
   a contact surface for contacting a body whose temperature is to be measured;
   wherein the first and second temperature sensors are arranged at different depths from the contact surface and the net thermal conductivity across the device from the contact surface through the first and second temperature sensors is greater than the net thermal conductivity of the device in lateral directions parallel to the contact surface;
   wherein a first material has an anisotropic thermal conductivity;
   wherein the thermal conductivity of the first material has an anisotropy ratio of at least 2.

2. A device as claimed in claim 1, wherein each depth is a distance from the contact surface to the respective temperature sensor along an axis substantially perpendicular to the contact surface.

3. A device as claimed in claim 1, wherein a surface of the first material component provides at least part of said contact surface.

4. A device as claimed in claim 1, wherein the net thermal conductivity across the device is lowest in the lateral directions.

5. A device as claimed in claim 1, wherein each depth is a thermal depth defined by the net thermal conductance from the contact surface to the respective temperature sensor.

6. A device as claimed in claim 5, wherein the first and second temperature sensors are at the same distance from the contact surface as measured in a direction along an axis substantially perpendicular to the contact surface.

7. A device as claimed in claim 1, wherein the first material comprises a first material component and a second material component, the first and second temperature sensors being embedded in the first material component, wherein the second material component at least partially encloses the first material component and has a lower thermal conductivity than the first material component.

8. A device as claimed in claim 7, wherein the first material component has a greater thermal conductivity than the second material component by a factor of at least 4.

9. A device as claimed in claim 7, wherein the second material component completely encloses the first material component.

10. A device as claimed in claim 9, wherein the second material component is thicker over the lateral extremities of the first material component than over the contact surface and its opposing surface.

11. A device as claimed in claim 7, wherein the first material component is substantially disc-shaped and the plane of the disc is substantially parallel to the contact surface.

12. A device as claimed in claim 11, wherein the second material component forms a ring-shaped annulus about the disc-shaped first material, the plane of the ring being substantially coincident with the plane of the disc.

13. A device as claimed in claim 7, wherein the first material component comprises at least first and second material parts having different thermal conductivities, the first temperature sensor being embedded in the first material part and the second temperature sensor being embedded in the second material part.

14. A device as claimed in claim 7, wherein the first material component is a thermally conductive polymer.

15. A device as claimed in claim 7, wherein, in use, a surface of the first material component remote from said contact surface is exposed.

16. A device as claimed in claim 15, wherein said remote surface supports a thin layer having a higher thermal conductivity than the first material.

17. A device as claimed in claim 7, wherein the first material component has a thermal conductivity of at least 0.5 W/mK.

18. A device, for measuring temperature comprising:
    first and second temperature sensors enclosed in a first material having a first material component and a second material component, the second material component at least partially enclosing the first material component and having a lower thermal conductivity than the first material component;
    wherein the first material component comprises at least first and second material parts having different thermal conductivities, the first temperature sensor being embedded in the first material part and the second temperature sensor being embedded in the second material part; and
    a contact surface for contacting a body whose temperature is to be measured;
    wherein at least part of the contact surface is provided by the first and second material parts.

* * * * *